United States Patent
Wheeler et al.

(10) Patent No.: US 9,120,712 B2
(45) Date of Patent: *Sep. 1, 2015

(54) PROCESS FOR IMPROVING THE ENERGY DENSITY OF FEEDSTOCKS USING FORMATE SALTS

(75) Inventors: Marshall Clayton Wheeler, Orono, ME (US); Adriaan R. P. van Heiningen, Orono, ME (US); Paige A. Case, Windham, ME (US)

(73) Assignee: UNIVERSITY OF MAINE SYSTEM BOARD OF TRUSTEES, Bangor, ME (US)

( * ) Notice: Subject to any disclaimer, the term of this patent is extended or adjusted under 35 U.S.C. 154(b) by 853 days.

This patent is subject to a terminal disclaimer.

(21) Appl. No.: 13/331,210

(22) Filed: Dec. 20, 2011

(65) Prior Publication Data

US 2012/0203043 A1    Aug. 9, 2012

Related U.S. Application Data

(60) Provisional application No. 61/438,419, filed on Feb. 1, 2011, provisional application No. 61/510,671, filed on Jul. 22, 2011.

(51) Int. Cl.
*C07C 1/00* (2006.01)
*C07C 1/207* (2006.01)
*C10G 3/00* (2006.01)

(52) U.S. Cl.
CPC ............. *C07C 1/2078* (2013.01); *C10G 3/40* (2013.01); *C10G 3/44* (2013.01); *C10G 2300/1014* (2013.01)

(58) Field of Classification Search
CPC .............. C10G 3/00; C10G 2300/101; C10G 2300/1011; C10G 17/10; C07C 7/00; C07C 7/04

USPC .......................... 585/240, 242; 560/155, 165
See application file for complete search history.

(56) References Cited

U.S. PATENT DOCUMENTS 5,969,189 A    10/1999    Holtzapple et al.
6,043,392 A     3/2000    Holtzapple et al.
(Continued)

FOREIGN PATENT DOCUMENTS

CN    1643116 A     7/2005
EP    2 025 735 A1  2/2009
(Continued)

OTHER PUBLICATIONS

Barth et al., "Motor Fuels From Biomass Pyrolysis", Chem. Eng. Technol., 31(5):773-781 (2008).
(Continued)

*Primary Examiner* — Nina Bhat
(74) *Attorney, Agent, or Firm* — Choate, Hall & Stewart, LLP; Brian E. Reese

(57) ABSTRACT

Methods of forming liquid hydrocarbons through thermal deoxygenation of cellulosic compounds are disclosed. Aspects cover methods including the steps of mixing a levulinic acid salt-containing feedstock with a formic acid salt, exposing the mixture to a high temperature condition to form hydrocarbon vapor, and condensing the hydrocarbon vapor to form liquid hydrocarbons, where both the formic acid salt and the levulinic acid salt-containing feedstock decompose at the high temperature condition and wherein one or more of the mixing, exposing, and condensing steps is carried out a pressure between about vacuum and about 10 bar.

16 Claims, 5 Drawing Sheets

(56) References Cited

U.S. PATENT DOCUMENTS

| | | | |
|---|---|---|---|
| 7,964,761 | B2 | 6/2011 | Zmierczak et al. |
| 2003/0233011 | A1* | 12/2003 | Fagan et al. .................... 560/174 |
| 2005/0171374 | A1* | 8/2005 | Manzer ......................... 560/190 |
| 2006/0047139 | A1* | 3/2006 | Ayoub ......................... 560/155 |
| 2007/0208183 | A1 | 9/2007 | Haan et al. |
| 2010/0312006 | A1 | 12/2010 | Lake et al. |
| 2010/0312028 | A1 | 12/2010 | Olson et al. |
| 2010/0324310 | A1 | 12/2010 | Dumesic et al. |
| 2011/0028773 | A1 | 2/2011 | Subramaniam et al. |
| 2011/0087058 | A1 | 4/2011 | Harlin et al. |
| 2011/0098490 | A1* | 4/2011 | Reunanen et al. ............ 549/498 |

FOREIGN PATENT DOCUMENTS

| | | |
|---|---|---|
| WO | 2007/099111 A1 | 9/2007 |
| WO | 2009/130387 A2 | 10/2009 |
| WO | WO-2010/141950 A2 | 12/2010 |
| WO | WO2010/141950 A2 | 12/2010 |

OTHER PUBLICATIONS

Gellerstedt et al., "Chemical Structures Present in Biofuel Obtained from Lignin", Energy & Fuels, 22:4240-4244 (2008).

Heeres et al., "Combined dehydration/(transfer)-hydrogenation of C6-sugars (D-glucose and D-fructose) to y-valerolactone using ruthenium catalysts", Green Chem., 11:1247-1255 (2009).

Kleinert et al., "Phenols from Lignin", Chem. Eng. Technol., 31(5):736-745 (2008).

Kleinert et al., "Towards a Lignincellulosic Biorefinery: Direct One-Step Conversion of Lignin to Hydrogen-Enriched Biofuel", Energy & Fuels, 22:1371-1379 (2008).

Kleinert et al., "Optimizing solvolysis conditions for integrated depolymerization and hydrodeoxygenation of lignin to produce liquid biofuel", J. Anal. Appl. Pyrolysis, 85:108-117 (2009).

Kleinert et al., "Developing Solvolytic Conversion of Lignin-to-Liquid (LtL) Fuel Components: Optimization of Qualilty and Process Factors", Cellulose Chem. Technol., 45(1-2):3-12 (2011).

Kopetzki et al., "Transfer hydrogenation of levulinic acid under hydrothermal conditions catalyzed by sulfate as a temperature-switchable base", Green Chem., 12:656-660 (2010).

Schwartz et al., "Energy densification of levulinic acid by thermal deoxygenation", Green Gemistry, 12:1353-1356 (2010).

International Search Report and the Written Opinion for PCT/US2011/066057, mailed Sep. 25, 2012.

International Preliminary Report on Patentability for PCT/US2011/066057, mailed Aug. 15, 2013.

Alonso, D.M. et al., Catalytic conversion of biomass to biofuels, Green Chemistry, 12(9):1493-1513 (2010).

Extended European Search Report for EP 11857902.8, 8 pages (Oct. 10, 2014).

Mehdi, H. et al., Integration of Homogeneous and Heterogeneous Catalytic Processes for a Multi-step Conversion of Biomass: From Sucrose to Levulinic Acid, γ-Valerolactone, 1,4-Pentanediol, 2-Methyl-tetrahydrofuran, and Alkanes, Topics in Catalysis, 48(1-4):49-54 (2008).

\* cited by examiner

PROCESS FOR IMPROVING THE ENERGY DENSITY OF FEEDSTOCKS USING FORMATE SALTS

CROSS-REFERENCE TO RELATED APPLICATIONS

This application claims priority under 35 U.S.C. §119 to U.S. Provisional Application No. 61/438,419, filed Feb. 1, 2011, and to U.S. Provisional Application No. 61/510,671, filed Jul. 22, 2011, which are herein incorporated by reference in their entirety.

GOVERNMENT RIGHTS STATEMENT

This invention was made with U.S. Government support under DE-FG-36-08GO18165 awarded by the Department of Energy; DE-FG02-07ER46373 awarded by the Department of Energy, Office of Experimental Program to Stimulate Competitive Research; and DE-FG02-08ER64635 awarded by the Department of Energy. The U.S. Government has certain rights in the invention.

TECHNICAL FIELD

The present invention generally relates to biomass-derived fuels. More particularly, the present invention relates to generating energy dense liquid fuels from biomass using levulinic acid or a levulinic acid salt and one or more formic acid salts.

BACKGROUND OF THE INVENTION

Global reliance on oil as a primary energy source has proven to be problematic. For the United States, with the price of oil increasing significantly in recent years and no indication of a trend reversal, the economic stability of the nation has come under intense scrutiny. One aspect of this scrutiny is on the current energy infrastructure and the need to find alternative sources of fuels.

While solar, wind and other technologies are being developed as alternative energy sources, the present automotive and aviation infrastructure currently requires liquid fuels. Accordingly, alternative ways to produce or improve liquid hydrocarbon-based fuels is highly desirable. Among the alternative fuel sources are biomass-derived liquid fuels. Biomass-derived liquid fuels are considered to be a sustainable and carbon-neutral source of liquid fuels and projections estimate that the United States has the potential to sustainably produce biomass sufficient to replace one-third or more of national petroleum consumption.

However, current methodologies only allow for the production of low energy density fuels. The low energy density of these fuels impacts the performance of vehicle and machinery powered by these fuels. What is needed are higher energy density fuels or methods of improving the energy density of currently produced biomass-derived liquid fuels.

SUMMARY OF THE INVENTION

Briefly, the present invention satisfies the need for higher energy density, biomass-derived fuels.

The present invention provides, in a first aspect, a method of forming liquid hydrocarbons (HC Oil), the method including the steps of mixing a levulinic acid salt-containing feedstock with a formic acid salt, exposing the mixture to a high temperature condition to form hydrocarbon vapor, and condensing the hydrocarbon vapor to form liquid hydrocarbons, wherein both the formic acid salt and the levulinic acid salt-containing feedstock decompose at the high temperature condition and wherein one or more of the mixing, exposing, and condensing steps is carried out at a pressure between about vacuum and about 10 bar.

The present invention provides, in a second aspect, a method of forming liquid hydrocarbons, the method comprising mixing a levulinic acid-containing feedstock with formic acid; neutralizing the mixture by adding one or more of: an alkali base, an alkaline earth base, and a base-forming metal oxide; exposing the neutralized mixture to a high temperature condition to form hydrocarbon vapor; and condensing said hydrocarbon vapor to form liquid hydrocarbons; wherein said neutralized mixture decomposes at said high temperature condition and wherein one or more of the mixing, exposing, and condensing steps is carried out at a pressure between about vacuum and about 10 bar.

These and other objects, features and advantages of this invention will become apparent from the following detailed description of the various aspects of the invention taken in conjunction with the accompanying drawings.

DETAILED DESCRIPTION OF THE INVENTION

Figure 1:
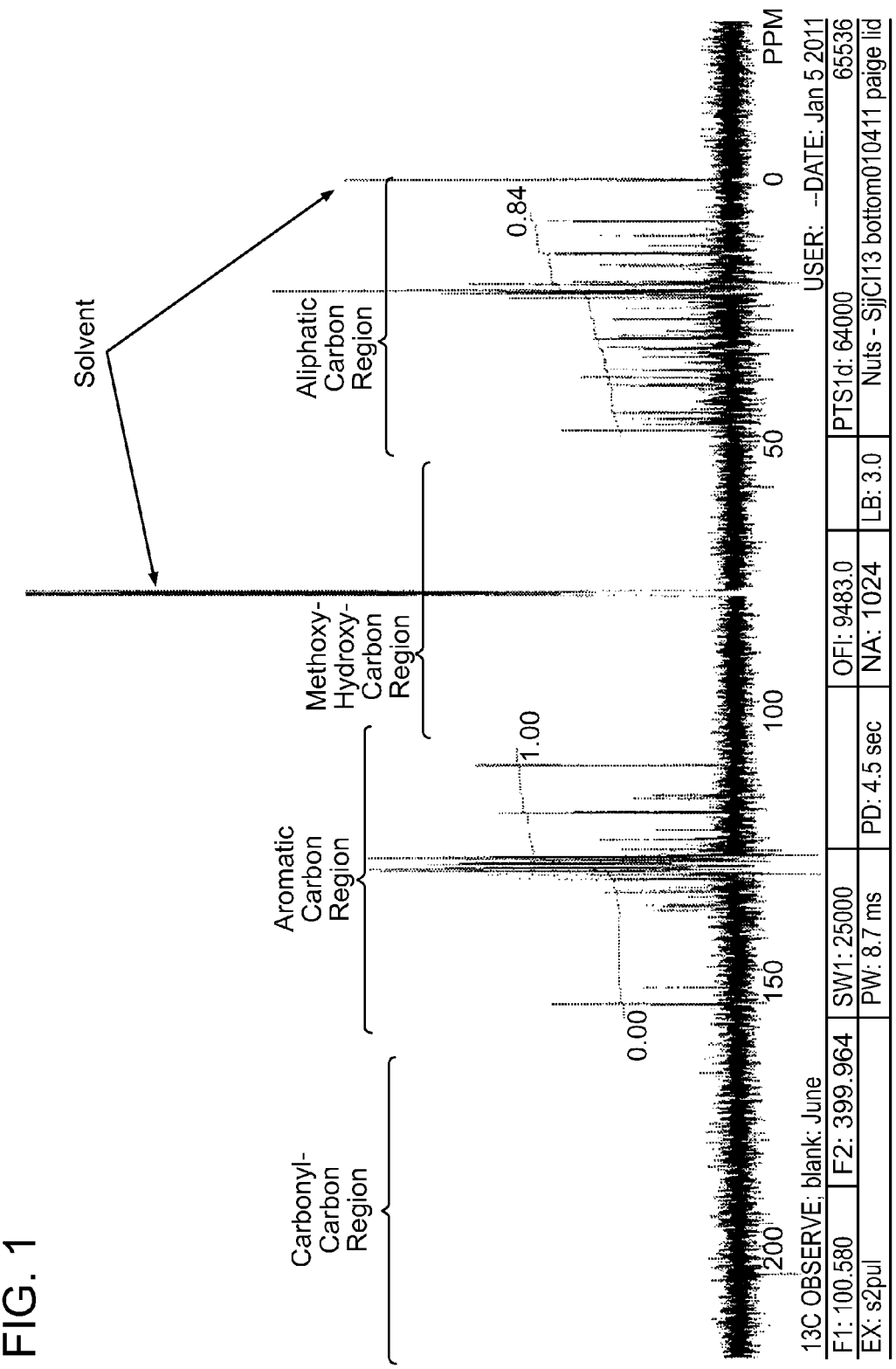
FIG. 1 shows the $^{13}C$ NMR spectrum of HC Oil produced according to the present invention, with no detectable oxygen-containing carbons.

The present invention provides, in a first aspect, a method of forming liquid hydrocarbons, the method including the steps of mixing a levulinic acid salt-containing feedstock with a formic acid salt, exposing the mixture to a high temperature condition to form hydrocarbon vapor, and condensing the hydrocarbon vapor to form liquid hydrocarbons, wherein both the formic acid salt and the levulinic acid salt-containing feedstock decompose at the high temperature condition and wherein one or more of the mixing, exposing, and condensing steps is carried out at a pressure between about vacuum and about 10 bar.

The term "levulinic acid salt-containing feedstock" as used herein means a solid or liquid feedstock comprising one or more salts of levulinic acid which could be produced from the neutralization of, for example, cellulosic biomass hydrolyzates including, but not limited to: hydrolyzates from cellulosic biomass, wood, wood waste, algal biomass, food waste, sludges and municipal solid waste. A wide array of levulinic acid salts are contemplated as within the scope of the processes of the present invention including, but not limited to, calcium levulinate, magnesium levulinate, sodium levulinate, potassium levulinate, lithium levulinate, zinc levulinate and mixtures thereof.

Various formic acid salts are contemplated as within the scope of the present invention. Non-limiting examples of acceptable formic acid salts include alkali formic acid salts, alkaline earth formic acid salts, formic acid salts of metals whose oxides form bases in water (so-called base-forming metal oxides), and mixtures thereof. More specific non-limiting examples include calcium formate, magnesium formate, sodium formate, potassium formate, lithium formate, zinc formate and mixtures thereof.

Several aspects of the present invention include a step of exposing a mixture of a feedstock and a formic acid salt to a high temperature condition. The specific temperature range will vary according to the specific embodiment being used in a particular application, as can be seen in the examples of this disclosure. Non-limiting temperature ranges include 200° C.-800° C., 200° C.-600° C., 375° C.-500° C., and 425° C.-525° C.

The length of time during which the mixture of feedstock and formic acid salt are exposed to a high temperature condition will vary according to the specifics of a particular application. The amount of material, presence or absence of other materials, and nature of desired end product may all affect the desired length of exposure to the high temperature condition. Non-limiting examples of exposure periods include from about one second to about four hours, from about one minute to about two hours, from about ten minutes to about two hours, and from about one hour to about two hours.

The present invention provides, in a second aspect, a method of forming liquid hydrocarbons, the method comprising mixing a levulinic acid-containing feedstock with formic acid; neutralizing the mixture by adding one or more of: an alkali base, an alkaline earth base, and a base-forming metal oxide; exposing the neutralized mixture to a high temperature condition to form hydrocarbon vapor; condensing said hydrocarbon vapor to form liquid hydrocarbons; wherein said neutralized mixture decomposes at said high temperature condition and wherein one or more of the mixing, neutralizing, exposing, and condensing steps is carried out at a pressure between about vacuum and about 10 bar.

The term "levulinic acid-containing feedstock" as used herein means a feedstock which could be produced by, for example, hydrolysis of cellulosic biomass including, but not limited to: hydrolyzates of cellulosic biomass, wood, wood waste, algal biomass, food waste, sludges and municipal solid waste.

Various bases are contemplated as within the scope of these aspects of the present invention. Non-limiting examples of acceptable bases include an alkali base, an alkaline earth base, or a base-forming metal oxide. More specific examples include, without limitation, hydroxides, carbonates, and oxides of calcium, magnesium, sodium, potassium, lithium, and zinc, and mixtures thereof.

Several of these aspects of the present invention include a step of exposing a mixture of a feedstock, formic acid and an alkali base, alkaline earth base, or base-forming metal oxide to a high temperature condition. The specific temperature range will vary according to the specific embodiment being used in a particular application, as can be seen in the examples of this disclosure. Non-limiting temperature ranges include 200° C.-800° C., 200° C.-600° C., 375° C.-500° C., and 425° C.-525° C.

The length of time during which the mixture of feedstock, formic acid and alkali base, alkaline earth base, or base-forming metal oxide are exposed to a high temperature condition will vary according to the specifics of a particular application. The amount of material, presence or absence of other materials, and nature of desired end product may all affect the desired length of exposure to the high temperature condition. Non-limiting examples of exposure periods include from about one second to about four hours, from about one minute to about two hours, from about ten minutes to about two hours, and from about one hour to about two hours.

Some aspects of the invention will include the generation of formic acid as a by-product of producing the levulinic acid-containing feedstock. In applications where this occurs, the levulinic acid-containing feedstock is considered to have been mixed with formic acid as a result of hydrolyzing the feedstock.

As used herein the terms "thermal deoxygenation" or "thermally deoxygenates" or the like mean one or more of several chemical reactions caused by exposure to high temperatures which result in the elimination of oxygen from and creation of new carbon-carbon bonds in the reaction products including ketonic decarboxylation, dehydration, condensation and free-radical reactions.

Unlike prior art methods of generating liquid fuels from biomass, the processes of the present invention may be carried out under completely dry, or substantially dry conditions and at moderate or even atmospheric pressures. Previously, reactions involving levulinic acid and formic acid or formate salts were carried out under aqueous conditions and under high pressure, and with the objective of forming γ-valerolactone rather than hydrocarbons.

The present invention improves upon the prior art in many ways. One way that many aspects of the invention improve over previously existing art is through being able to generate energy dense liquid hydrocarbons without the need for modulated pressure. Many aspects of the present invention, including many of those exemplified in this disclosure, are carried out at atmospheric pressure and do not require the special equipment and/or conditions that previously existing processes do. It is contemplated as within the scope of the present invention that aspects will be carried out at a range of pressures, such as, for example, vacuum conditions up to pressures of about 10 bar. Additional ranges that may be desirable for particular applications include, but are not limited to, about zero bar to about 10 bar, about 1 bar to about 8 bar, about 1 bar to about 5 bar, about 1 bar to about 3 bar, and about 1 bar to about 2 bar.

Generally, several aspects of the present invention include a new process for making a liquid hydrocarbon called HC Oil, which exhibits a heating value of >40 MJ/kg, from carbohydrate-containing feedstocks which include cellulosic biomass, wood, wood waste, algal biomass, food waste, sludges and municipal solid waste. Surprisingly, it was discovered that the addition of formic acid in proper proportions to levulinic acid prior to thermal deoxygenation may result in a hydrocarbon product that phase separates with water. Aspects of the invention may be used to produce a variety of liquid hydrocarbons including, but not limited to petrochemicals, diesel, kerosene, gasoline, and jet fuel. Hydrocarbon oils produced by the process described herein may not need upgrading or further processing for many applications, including, but not limited to, blending with diesel, heating oil, or as a component of bio jet fuel.

The present invention represents a significant improvement over the prior art because several of the present methods may be performed in relatively high yields and are robust in that they do not require any precious metal catalysts, unlike prior methods of generating liquid hydrocarbons. In fact, unlike previous methods, the process disclosed herein does not require any externally added hydrogen to facilitate deoxygenation of the feedstock. In addition, the process disclosed herein is tolerant of impurities which may be present in levulinic acid or levulinic acid salt feedstocks, including but not limited to, water, unconverted carbohydrates, lignin, chars, tars, humins, chloride, and sulfate, unlike previous methods of generating liquid hydrocarbons. These methods incorporate a robust reaction that can use a variety of raw materials to provide the required levulinic acid-containing feedstock or levulinic acid salt-containing feedstock, including producing HC Oil from raw levulinic acid that was derived from municipal solid wastes or food waste, for example.

Other aspects of the invention include integration of the HC Oil Process within the lime cycle in a pulp mill in order to improve the operability and energy efficiency, and decrease capital costs of the HC Oil Process.

In general terms, several aspects of the invention involve converting carbohydrates in a solid feedstock to levulinic acid, neutralizing the levulinic acid with a cationic compound, such as, for example, either $Ca(OH)_2$ or $Mg(OH)_2$, drying the resulting levulinate salt, and heating the salt to a temperature sufficient to decompose the salt into a hydrocarbon product, for example, 450° C. Surprisingly, the present inventors found that adding formic acid to the levulinic acid feed, even with as low as 0.05/1 formic acid/levulinic acid molar ratio, improves the thermal deoxygenation (TDO) chemistry significantly and results in a non-aqueous hydrocarbon product that contains no oxygen-containing compounds that are detectable by NMR as shown in FIG. 1. Previous methods for producing hydrocarbons from levulinic acid produced products that were water soluble and would have required catalytic upgrading to make them fungible fuel components.

Aspects of the invention may vary in the specific inorganic cationic compound used to neutralize levulinic acid and formic acid. Any application-appropriate inorganic cationic compound may be used, for example, calcium, magnesium, sodium, potassium, zinc, copper, iron, or lithium-containing compounds. Non-limiting examples of such compounds include hydroxides, carbonates, and oxides of calcium, magnesium, sodium, potassium, lithium, zinc and combinations thereof.

Embodiments of the present invention produce a range of hydrocarbon yields. A non-limiting example of hydrocarbon yields within the scope of the invention include, for example, a yield of approximately 40% of the theoretical maximum yield using a 0.05/1 ratio of formic acid to levulinic acid, to a yield of approximately 80% of the theoretical maximum yield using a 1/1 ratio. In order to estimate the theoretical maximum yield, the stoichiometry of the TDO reaction may be approximated by

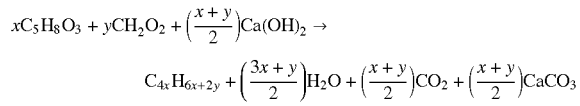

Figure 2:
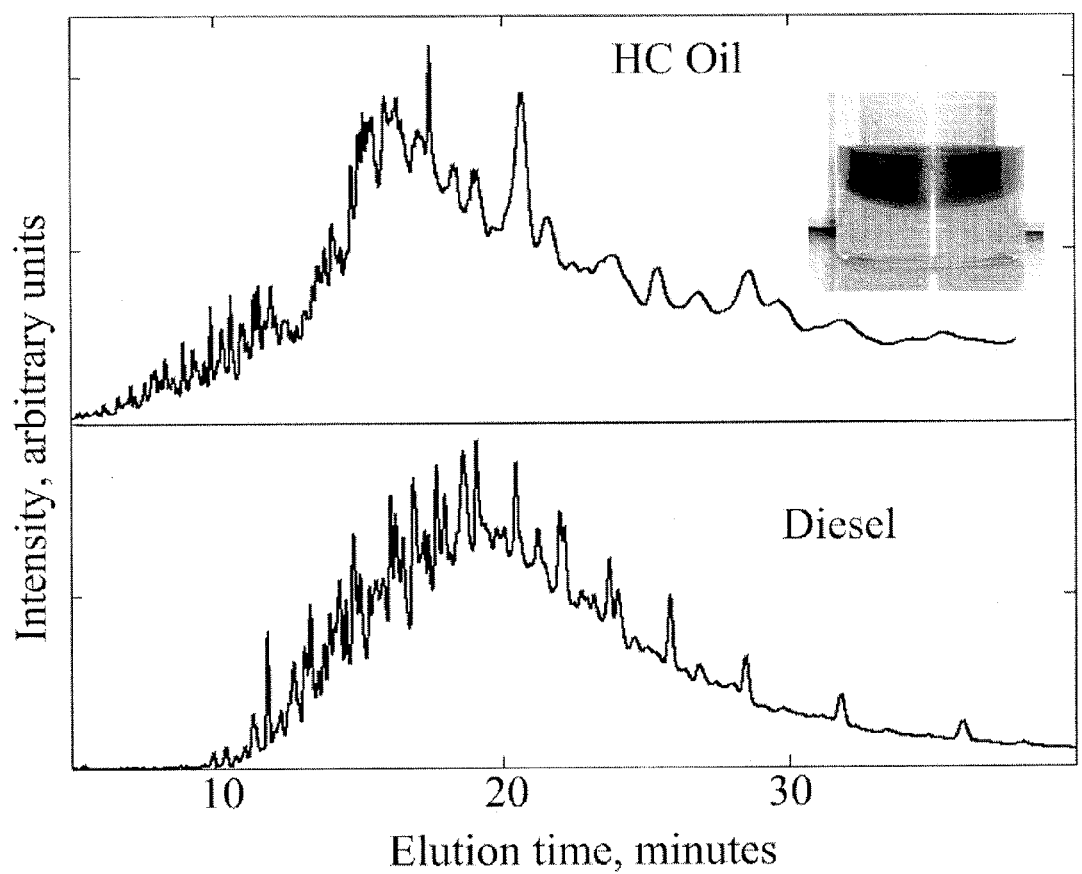
FIG. 2 depicts a gas chromatogram of HC Oil (top) produced according to the present invention compared to a diesel standard (bottom). Unrefined HC Oil is immiscible in water (inset).

FIG. 2 shows a gas chromatogram comparing HC Oil to a diesel standard. The volatility of HC Oil appears to be similar to a "light diesel" or kerosene with a small fraction of lighter gasoline-like components as shown in FIG. 2. HC Oil produced according to aspects of the present invention may be completely miscible with diesel, but not in water, as shown in the inset in FIG. 2. If it is necessary to improve HC Oil's combustion properties, HC Oil could therefore be blended with gasoline, diesel, jet fuel, or kerosene. A fractional distillation is one exemplary process that would allow for separation of appropriate fractions.

Figure 3:
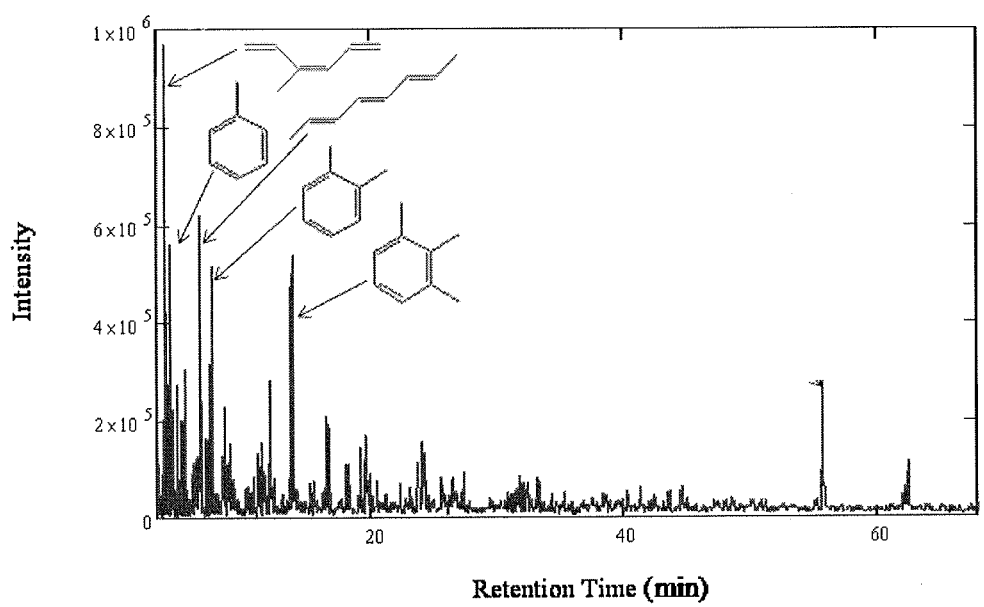
FIG. 3 shows a gas chromatogram with some of the major components of HC Oil produced according to the present invention identified by their mass spectra.

Some of the major products in HC Oil produced according to the present invention have been identified using gas chromatography/mass spectrometry. An exemplary chromatogram is shown in FIG. 3. In addition to the identified products, some naphthalene may be observed at a longer elution time in certain applications.

The TDO reaction may be converted to a continuous process by adapting fluid-bed or auger pyrolysis reactor technologies. In contrast to HC Oil, pyrolysis oils still typically contain mostly oxygen-containing compounds including phenolics, carbohydrates, and organic acids. Therefore pyrolysis oils have HHV of approximately 25 to 35 MJ/kg, typically have very low pH (~2-4) and the reactive functional groups tend to cause polymerization and therefore significantly increase the viscosity of the oil in just a few months at room temperature. Many of the components of pyrolysis oils are also water soluble, so they often contain up to 30 wt % water. Known pyrolysis oil upgrading schemes require significant hydrogen for removal of the oxygen-containing functionalities as water. One of the several benefits of the present invention is that exogenous hydrogen is not required for deoxygenation.

EXAMPLES

Example 1

Conceptual Example of Process

Figure 4:
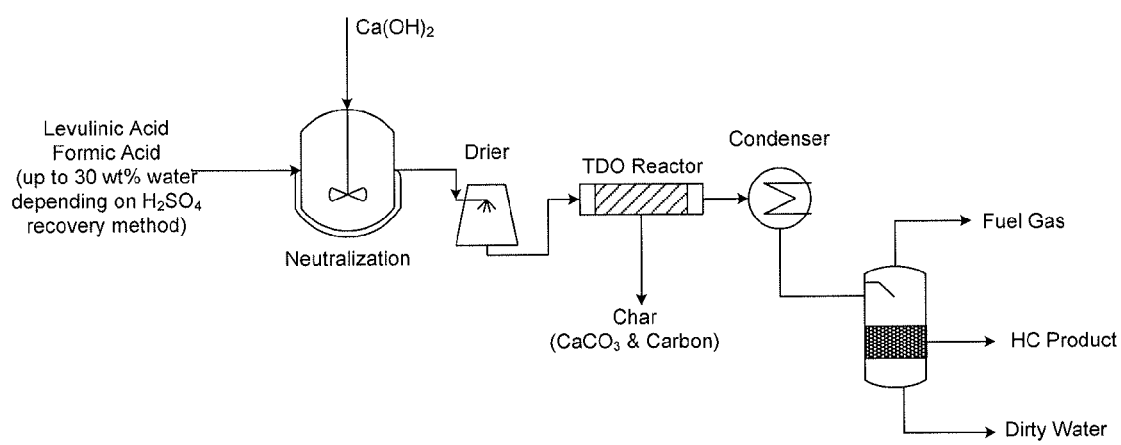
FIG. 4 depicts a general conceptual process flow diagram of a levulinic acid thermal deoxygenation process according to aspects of the present invention.

A conceptual process flow diagram for converting an organic acid, here levulinic acid, to hydrocarbons is shown in FIG. 4. Levulinic acid is mixed with an application-appropriate quantity of formic acid. The specific amount and concentration of formic acid may be determined by the parameters of the specific application of the invention, including, for example, the yield of hydrocarbon product desired or expected as an outcome of the TDO process.

In this example, levulinic acid is first neutralized by a stoichiometric quantity of an application-appropriate inorganic cationic compound, here calcium hydroxide $(Ca(OH)_2)$. The mixture is then heated, such as in a TDO reactor, to a temperature sufficient to evaporate water from the mixture, for example, to 200° C. The mixture is held at the raised temperature for an application-appropriate period of time, for example, 5 minutes. At this temperature, a significant quantity of any water present in the mixture evaporates. As an example, the water may consist of excess water in the acid feed and the water that was released during salt formation according to the following equation:

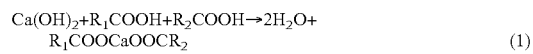

where $R_1$ and $R_2$ may be either H for formic acid or $C_4H_7O$ for levulinic acid, though these are merely illustrative examples. The reactor temperature may then be increased to a level sufficient to decompose the salt resulting from the neutralization of the feedstock organic acid (here levulinic acid), for example, 450° C. for a period of about 30 minutes. As the reactor temperature approaches 450° C., the salt decomposes by a ketonization mechanism

When the R-groups are aliphatic, the products of reaction 2 are primarily ketones with high yields. However, if the R-groups contain carbonyl functional groups, such as in levulinic acid, the carbonyl groups in the product of reaction 1 promote additional aldol condensation reactions which effectively remove the oxygen from the molecules as water. For the purposes of this disclosure, the combination of reaction 1 and the subsequent aldol condensation reactions are referred to as thermal deoxygenation (TDO). The calcium hydroxide in reaction 1 can be regenerated by a lime cycle

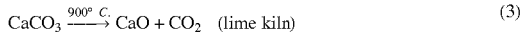

$$CaCO_3 \xrightarrow{900°\ C.} CaO + CO_2 \quad \text{(lime kiln)} \tag{3}$$

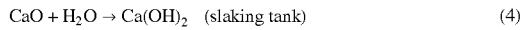

$$CaO + H_2O \rightarrow Ca(OH)_2 \quad \text{(slaking tank)} \tag{4}$$

It has been demonstrated that, with the proper reactor configuration (such as an auger pyrolysis reactor or modified gasifier system), it is possible to feed the wet salts directly to the TDO reactor. For this case, the theoretical stoichiometry of the TDO reactor can be approximated by the following equation:

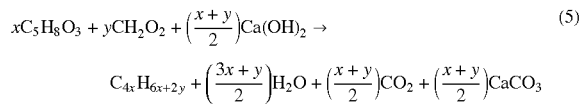

$$xC_5H_8O_3 + yCH_2O_2 + \left(\frac{x+y}{2}\right)Ca(OH)_2 \rightarrow$$
$$C_{4x}H_{6x+2y} + \left(\frac{3x+y}{2}\right)H_2O + \left(\frac{x+y}{2}\right)CO_2 + \left(\frac{x+y}{2}\right)CaCO_3 \tag{5}$$

A condenser may then be used to distill the TDO products into usable forms including, for example, fuel gas and other hydrocarbon products (HC product) and waste products, including dirty water as shown in FIG. 4.

Exemplary non-condensable components generated by aspects of the present invention include $CO_2$, $CO$, $CH_4$, $H_2$, ethylene, propane and butane, as well as other unidentified compounds.

Example 2

Hydrocarbon Production from Mixtures of Formic Acid and Levulinic Acid

Figure 5:
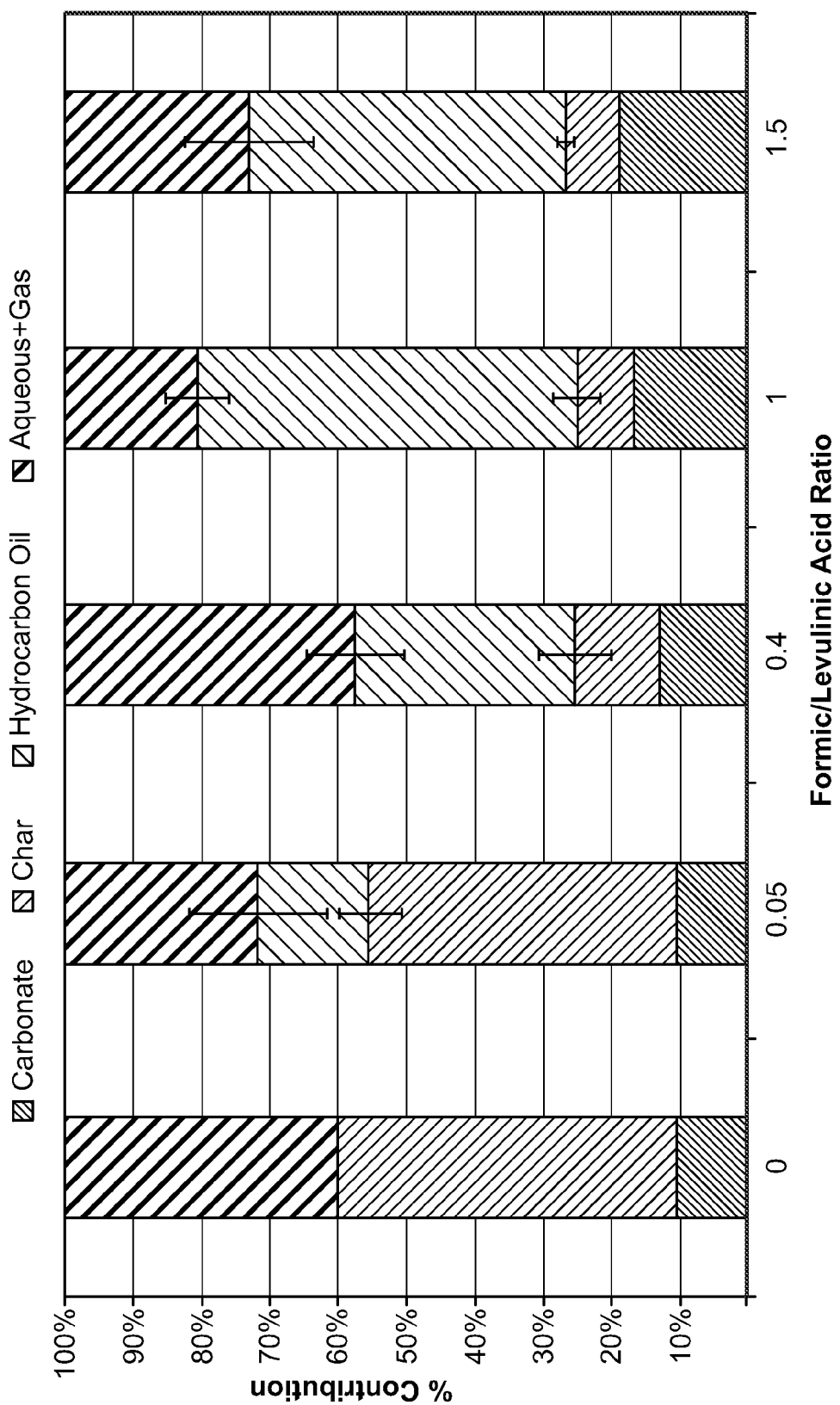
FIG. 5 shows a graph of some of the organic products resulting from aspects of the present invention.

Experiments were conducted to demonstrate the effect of adding formic acid during the thermal deoxygenation of levulinic acid. Reactions were conducted by adding organic acids and an alkaline earth base to a stirred 300 mL semibatch reactor along with stainless steel ball bearings to aid in material mixing. Reagent grade $Ca(OH)_2$ (>98%), levulinic acid (>99%), and formic acid (>95%) were added the reactor, and the liquid mixture was stirred. 20% excess $Ca(OH)_2$ was used for each of the experiments. Nitrogen was continually swept through the reactor at a rate of 100 SCCM, and the products were continuously condensed in a condenser (10° C.), while non-condensable products were collected in bags. Vapors evolved over the course of a 10° C./min temperature ramp from room temperature to 450° C. The temperature was then maintained constant at 450° C. until no additional product evolution was observed. FIG. 5 shows that when levulinic acid was the only organic acid in the mixture, the organic products of TDO were soluble in the water which was also evolved during the reaction. However, when formic acid was present in the reaction mixture, a hydrocarbon oil was formed which phase separated from the aqueous components. The lower error bars represent the standard deviations in the combined masses of carbonaceous char and calcium carbonate residue in the reactor after the experiments. The upper error bars represent the standard deviations in the mass of hydrocarbon oil which was decanted from the condensed aqueous phase. The organic carbon in the aqueous and gas fractions were calculated by difference. As the ratio of formic acid to levulinic acid was increased, the proportion of oil increased. Furthermore, the presence of formic acid decreased the quantity of carbonaceous char in the residue. The highest yield of hydrocarbon oil was for a formate/levulinate mole ratio of 1/1.

$C^{13}$ Nuclear magnetic resonance (NMR) was used to analyze the hydrocarbon products. FIG. 1 is a typical spectrum in which regions of carbon functionality are indicated. Note that the hydrocarbon oil has almost no oxygenated carbons.

Table 1 was generated from the data for the experiments in FIG. 5 using bomb calorimetry, CHNO analysis, and $C^{13}$ NMR. The table shows that the addition of formate increases the higher hating value of levulinic acid TDO products, even at formic/levulinic acid mole ratios as low as 1/20. Furthermore, the composition of the hydrocarbon oil can be varied by changing the formic/levulinic acid ratio. Note that the degree of hydrogen saturation of the oil decreases as the formic/levulinic acid ratio increases.

TABLE 1

| Formic/ Levulinic Acid Ratio (molar) | Higher Heating Value (MJ/kg) | Hydrogen/ Carbon Ratio (mol/mol) | % Alkyl Carbon Area $^{13}$C NMR | % Aromatic/ Alkene Carbon Area $^{13}$C NMR |
|---|---|---|---|---|
| $0^a$ | 35 | — | 40 | 44 |
| 1/20 | 39.5 | 1.21 | 57.1 | 41.7 |
| 1/2.5 | 40.9 | 1.35 | 44.4 | 55.5 |
| 1/1 | 40.7 | 1.27 | 38.2 | 61.5 |
| 1.5/1 | 41.3 | 1.29 | 38.8 | 60.9 |

$^a$Results of organic mixture which was extracted from the aqueous phase since no oil layer was formed

Example 3

Hydrocarbon Production from Mixed Formate and Levulinate Salts

Experiments were conducted to show that hydrocarbon oil can be produced starting with mixtures of dry salts. Salts were prepared by mixing 550 g $Ca(OH)_2$, 550 g $H_2O$, 703 g levulinic acid, 307 g formic acid. The slurry was dried under ambient conditions, and the dried salt was crushed into particles with sizes up to approximately 5 cm diameter. Approximately 1 kg of dried salt was added to a 3 L, stirred, semibatch reactor in which the temperature was ramped from room temperature to about 500° C. over approximately 3 hours. The reactor was continually purged with nitrogen at a flow rate of 0.5 SLPM, and the products were continuously condensed by a condenser (1° C.) followed by an electrostatic precipitator. The yield of hydrocarbon oil ranged from 0.13 to 0.15 kg oil/kg of salt fed. The hydrocarbon oil properties and composition were similar to those in Example 1.

Example 4

Continuous Thermal Deoxygenation of Dry Salts of Calcium Formate and Calcium Levulinate An experiment was conducted to show that hydrocarbon oil could be formed by feeding dry organic acid salts continuously into a reaction vessel which was maintained at a constant temperature. Salts were prepared in the same manner as in Example 2. The dry salts were fed to a 2.5 L, wiped-surface, horizontal reactor at a rate of 0.25 kg/hr. The reactor was continually purged with nitrogen at a flow rate of 0.5 SLPM. The solids were continuously collected in a bunker, and the vapors were continuously condensed by a condenser (15° C.). A hydrocarbon oil was collected which had properties and composition similar to those in Example 1.

Example 5

Thermal Deoxygenation of Sodium, Magnesium, and Potassium Salts

Experiments were conducted to demonstrate that basic cations, other than calcium, can also be used to produce hydrocarbon oils from mixtures of formic acid and other organic acids. 125 g $Mg(OH)_2$, 235 g levulinic acid, 103 g formic acid, and 200 g water were added to a 3 L, stirred, semibatch reactor. The reactor temperature was ramped from room temperature to 475° C. over approximately 3 hours. Nitrogen was swept through the reactor at a flow rate of 0.5 SLPM, and the vapors were condensed in a 1° C. condenser followed by an electrostatic precipitator. 81 g of hydrocarbon oil were collected. Another experiment was conducted with 164 g NaOH, 234 g levulinic acid, 102 g formic acid, and 281 g water which produced 80 g of hydrocarbon oil. Another experiment was conducted starting with 476 g KOH, 351 g levulinic acid, 152 g formic acid, and 550 g water which produced 60 g of hydrocarbon oil.

Example 6

Thermal Deoxygenation of a Mixture of Calcium Formate and Calcium Levulinate

An experiment was conducted to show that hydrocarbon oil can be produced by thermal deoxygenation of a mixture of organic acid salts which had been formed separately. Calcium formate was prepared by mixing 74 g $Ca(OH)_2$ and 92 g formic acid in 0.5 L of water. The calcium formate mixture was then dried in an oven at 100° C. Calcium levulinate was prepared by mixing 74 g $Ca(OH)_2$ and 232 g levulinic acid in 1 L of water. The calcium levulinate mixture was then dried in an oven at 100° C. 101 g of the dried calcium formate salt was added to a 3 L, stirred, semibatch reactor. Nitrogen was swept through the reactor at a flow rate of 0.5 SLPM, and the vapors were condensed in a 1° C. condenser followed by an electrostatic precipitator. The reaction produced 37 g of hydrocarbon oil.

Example 7

Thermal Deoxygenation of Crude Organic Acid Mixture which was Produced from Lignocellulosic Biomass An experiment was conducted using a crude mixture of biomass-derived levulinic acid, which also contained formic acid along with other hydrolysis process impurities such as water, unconverted carbohydrates, sodium, potassium, chloride, sulfate, sodium and magnesium. 100 g of formic acid was added to 500 g of the crude levulinic acid. The salt mixture was neutralized with 190 g $Ca(OH)_2$ and 200 g water, then dried at room temperature. 870 g of the solid salts (ca 20% moisture) was added to a 3 L, stirred, semibatch reactor. Nitrogen was swept through the reactor at a flow rate of 0.5 SLPM, and the vapors were condensed in a 1° C. condenser followed by an electrostatic precipitator. The reaction produced 86 g of hydrocarbon oil.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

The invention claimed is:

1. A method of forming liquid hydrocarbons, the method comprising
    mixing a levulinic acid salt-containing feedstock with a formic acid salt;
    exposing the mixture to a high temperature condition between 200° C. and 600° C., inclusive, to form hydrocarbon vapor; and condensing said hydrocarbon vapor to form liquid hydrocarbons;
    wherein both said formic acid salt and said levulinic acid salt-containing feedstock decompose at said high temperature condition and wherein one or more of the mixing, exposing, and condensing steps is carried out at a pressure between about vacuum and about 10 bar.

2. The method of claim 1, wherein said formic acid salt is selected from the group consisting of an alkali formic acid salt, an alkaline earth formic acid salt, a base-forming metal oxide, and mixtures thereof.

3. The method of claim 2, wherein said formic acid salt is selected from the group consisting of: calcium formate, magnesium formate, sodium formate, potassium formate, lithium formate, zinc formate, and mixtures thereof.

4. The method of claim 1, wherein said high temperature condition is between about 375° C. and about 500° C.

5. The method of claim 1, wherein said mixture is exposed to said high temperature condition for an extended period of time.

6. The method of claim 5, wherein said extended period of time is between about one second and about four hours.

7. The method of claim 1, wherein said levulinic acid salt-containing feedstock is selected from the group consisting of: calcium levulinate, magnesium levulinate, sodium levulinate, potassium levulinate, lithium levulinate, zinc levulinate and mixtures thereof.

8. The method of claim 1, wherein said levulinic acid salt-containing feedstock is selected from the group consisting of calcium levulinate, magnesium levulinate, sodium levulinate, and potassium levulinate, and said formic acid salt is selected from the group consisting of calcium formate, magnesium formate, sodium formate, and potassium formate.

9. The method of claim 1, wherein one or more of the mixing and exposing steps are carried out with substantially no aqueous component.

10. A method of forming liquid hydrocarbons, the method comprising
    mixing a levulinic acid-containing feedstock with formic acid;
    neutralizing the mixture by adding one or more of: an alkali base, an alkaline earth base, and a base-forming metal oxide;
    exposing the neutralized mixture to a high temperature condition between 200° C. and 600° C., inclusive, to form hydrocarbon vapor; and
    condensing said hydrocarbon vapor to form liquid hydrocarbons;
    wherein said neutralized mixture decomposes at said high temperature condition and wherein one or more of the mixing, neutralizing, exposing, and condensing steps is carried out at a pressure between about vacuum and about 10 bar.

11. The method of claim 10, wherein said alkali base, alkaline earth base or base-forming metal oxide is selected from the group consisting of: hydroxides, carbonates, and oxides of calcium, magnesium, sodium, potassium, lithium, and zinc, and mixtures thereof.

12. The method of claim 10, wherein said formic acid is present and mixed with said levulinic acid-containing feedstock as a result of producing said levulinic acid-containing feedstock.

13. The method of claim 10, wherein said high temperature condition is between about 375° C. and about 500° C.

14. The method of claim 10, wherein said neutralized mixture is exposed to said high temperature condition for an extended period of time.

15. The method of claim 14, wherein said extended period of time is between about one second and about four hours.

16. The method of claim 10, wherein said levulinic acid-containing feedstock is selected from hydrolyzates selected from the group consisting of: cellulosic biomass, wood, wood waste, algal biomass, food waste, sludges and municipal solid waste, and mixtures thereof.

\* \* \* \* \*